(12) United States Patent
Tighe et al.

(10) Patent No.: US 7,875,020 B2
(45) Date of Patent: Jan. 25, 2011

(54) STERILE DOCKING APPARATUS AND METHOD

(75) Inventors: Gerry Tighe, West Long Branch, NJ (US); Brian Eugene Baldwin, Centennial, CO (US); Joseph V. Ranalleta, Englewood, CO (US)

(73) Assignee: Baxa Corporation, Englewood, CO (US)

( * ) Notice: Subject to any disclaimer, the term of this patent is extended or adjusted under 35 U.S.C. 154(b) by 0 days.

(21) Appl. No.: 12/467,873

(22) Filed: May 18, 2009

(65) Prior Publication Data

US 2009/0306628 A1    Dec. 10, 2009

Related U.S. Application Data

(60) Continuation of application No. 11/433,064, filed on May 10, 2006, now abandoned, and a division of application No. 10/226,183, filed on Aug. 22, 2002, now Pat. No. 7,081,109.

(51) Int. Cl.
*A61M 39/18* (2006.01)

(52) U.S. Cl. ....................................................... 604/539

(58) Field of Classification Search ................. 604/538, 604/539, 263, 246, 533, 256; 251/149, 149.1–149.5, 251/149.7–149.9
See application file for complete search history.

(56) References Cited

U.S. PATENT DOCUMENTS

| 4,411,656 A | 10/1983 | Cornett, III |
| 4,534,573 A | 8/1985 | Somers |
| 4,597,758 A | 7/1986 | Aalto et al. |
| 5,167,643 A | 12/1992 | Lynn |
| 5,265,822 A | 11/1993 | Shober, Jr. et al. |

(Continued)

FOREIGN PATENT DOCUMENTS

EP    0716860    6/1996

(Continued)

OTHER PUBLICATIONS

OPIT Source Book, Feb. 2001 Edition, by Abbott Laboratories, The LifeShield, Clave and Connector Family, www.optisourcebook.com, 5 pages.

*Primary Examiner*—Kevin C Sirmons
*Assistant Examiner*—Michael J Anderson
(74) *Attorney, Agent, or Firm*—Marsh Fischmann & Breyfogle LLP

(57) ABSTRACT

The present invention provides an inventive apparatus and method for docking of a male luer connector fluidly interconnected or interconnectable to a medical liquid source during one or repeated periods. As such, the invention has particular application to multiple-dose medication therapy procedures. The docking apparatus comprises a holding receptacle having a single access opening and a depressible member disposed in the holding receptacle. The holding receptacle is adapted for retentive engagement with a male luer connector (e.g. via complementary threading), wherein upon docking a nozzle of the male luer connector is isolated within the holding receptacle. An anti-bacterial material may be readily applied to a top surface of the depressible member prior to docking so that the forward edge of the nozzle of the male luer connector contacts the anti-bacterial material when docked. The docking apparatus may be provided with lateral and rearward handling members to facilitate docking procedures. Additionally, slots may be provided for interconnecting the docking apparatus to a tubing line at a patient site.

22 Claims, 8 Drawing Sheets

U.S. PATENT DOCUMENTS

| | | |
|---|---|---|
| 5,295,957 A | 3/1994 | Aida et al. |
| 5,514,117 A | 5/1996 | Lynn |
| 5,524,783 A | 6/1996 | Popoff |
| 5,535,785 A | 7/1996 | Werge et al. |
| 5,620,427 A | 4/1997 | Werschmidt et al. |
| 5,676,346 A | 10/1997 | Leinsing |
| 5,681,279 A | 10/1997 | Roper et al. |
| 5,699,821 A | 12/1997 | Paradis |
| 5,702,374 A | 12/1997 | Johnson |
| 5,730,723 A | 3/1998 | Castellano et al. |
| 5,775,671 A | 7/1998 | Cote, Sr. |
| 5,782,816 A | 7/1998 | Werschmidt et al. |
| 5,788,215 A | 8/1998 | Ryan |
| 5,807,345 A | 9/1998 | Grabenkort |
| 5,820,602 A | 10/1998 | Kovekman et al. |
| 5,851,201 A | 12/1998 | Ritger et al. |
| 5,855,230 A | 1/1999 | Guala et al. |
| 5,947,954 A | 9/1999 | Bonaldo |
| 5,954,313 A | 9/1999 | Ryan |
| 5,984,373 A | 11/1999 | Fitoussi et al. |
| 6,032,926 A | 3/2000 | Fuchs |
| 6,039,302 A | 3/2000 | Cote, Sr. et al. |
| 6,063,062 A | 5/2000 | Paradis |
| 6,152,913 A | 11/2000 | Feith et al. |
| 6,158,458 A | 12/2000 | Ryan |
| 6,171,287 B1 | 1/2001 | Lynn et al. |
| 6,171,484 B1 | 1/2001 | Schnell et al. |
| 6,217,560 B1 | 4/2001 | Ritger et al. |
| RE37,357 E | 9/2001 | Lynn |
| 6,332,633 B1 | 12/2001 | Fitoussi et al. |
| 6,394,983 B1 | 5/2002 | Mayoral et al. |
| RE38,145 E | 6/2003 | Lynn |
| 6,732,872 B1 | 5/2004 | Grego et al. |
| 6,985,870 B2 | 1/2006 | Martucci et al. |
| 7,033,339 B1 | 4/2006 | Lynn |
| 7,081,109 B2 | 7/2006 | Tighe et al. |
| RE39,334 E | 10/2006 | Lynn |
| 2002/0193752 A1 | 12/2002 | Lynn |
| 2004/0039374 A1 | 2/2004 | Tighe et al. |
| 2006/0129112 A1 | 6/2006 | Lynn |
| 2006/0271000 A1 | 11/2006 | Ranalletta et al. |
| 2008/0048144 A1 | 2/2008 | Lynn |
| 2008/0051733 A1 | 2/2008 | Lynn |

FOREIGN PATENT DOCUMENTS

| | | |
|---|---|---|
| WO | WO0193936 | 12/2001 |

STERILE DOCKING APPARATUS AND METHOD

CROSS-REFERENCE TO RELATED APPLICATIONS

This application is a continuation application of U.S. patent application Ser. No. 11/433,064 filed May 11, 2006, which is a divisional application of U.S. patent application Ser. No. 10/226,183 filed Aug. 22, 2002, now U.S. Pat. No. 7,081,109, issued on Jul. 25, 2006. Each of the foregoing is incorporated herein by reference in its entirety.

FIELD OF THE INVENTION

The present invention relates to the field of medical liquid administration, and more particularly, to a docking apparatus and method for enhancing the maintenance of sterility of a male luer connector fluidly interconnected or interconnectable to a medical liquid source during one or repeated periods of non-use (e.g. between successive administrations of a medical liquid through a vascular catheter over an extended time period).

BACKGROUND OF THE INVENTION

Numerous techniques are employed for the administration of "medical liquids" (e.g. liquid medication and flush solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy. By way of example, the time period between IV drug infusions may be between about 4 to 24 hours, wherein the IV liquid medication source is typically replaced after each dose infusion. In the course of extended medication therapy a given tubing line set may be repeatedly employed, and a number of tubing line sets may be successively employed. For example, it is typical to replace a given tubing line set every two or three days.

In conjunction with extended therapy applications, a desirable practice is to disconnect a vascular catheter from a medical liquid source/tubing line set between infusions. In this regard, most patients receiving IV medication therapy are ambulatory to some degree and benefit from not being continuously connected to a medical liquid source/tubing line set.

To facilitate the ready and repeated connection/disconnection of a vascular catheter and medical liquid source/tubing line set, while avoiding the use of needle-type arrangements (e.g. arrangements where sharp/blunt needle ends are inserted into specialized vascular catheter connection ports having a pierceable/slit stopper), complimentary female and male luer connectors are often utilized. That is, a female luer connector is fluidly interconnected as an access port to the vascular catheter and a complimentary male luer connector is fluidly interconnected or readily interconnectable to the medical liquid source as part of the associated tubing line set. In order to maintain sterility, the male luer connector is typically covered with a new cap after each disconnection from the female luer connector, and the female luer connector is contacted with an antibacterial material (e.g. an alcohol solution) before each interconnection with the male luer connector. Such an approach entails the unpackaging, use and disposal of multiple caps over an extended medication therapy. For example, where liquid medication is administered at least every four hours over a three-day period at least 18 caps would be required to maintain the sterility of the male luer connector. As may be appreciated, cap-related costs, medical personnel time expenditures and inventory management implications associated with this approach can become quite significant.

SUMMARY OF THE INVENTION

In view of the foregoing, a broad objective of the present invention is to facilitate both the sterile and cost-effective handling of male luer connectors that are repeatedly interconnected/disconnected in the course of medical treatment, particularly in applications where multiple vascular catheter interconnections/disconnections with a medical liquid source are entailed in the course of IV medication therapy.

A further goal of the present invention is to address the noted broad objective in a manner that actually reduces medical accessory costs, inventory management requirements and medical personnel time expenditures.

Yet another objective of the present invention is to provide for enhanced sterile handling of male luer connectors fluidly interconnected or interconnectable to medical liquid sources in a manner that is both convenient and space-efficient at a patient care site.

One or more of the above objectives and additional advantages are realized by the inventive apparatus and method disclosed herein. In particular, a dedicated apparatus is provided for docking a male luer connector that is fluidly interconnected or interconnectable to a medical liquid source during one or repeated periods of non-use. The apparatus comprises a holding receptacle, adapted for selective retentive engagement with a male luer connector, and a depressible member disposed in an internal chamber of the holding receptacle. More particularly, a top end of the depressible member is located in a single access opening to the internal chamber, wherein a nozzle of a male luer connector may be inserted into the single access opening to contact and depress the depressible member while being isolated inside the holding receptacle. In short, a simple yet effective apparatus of a dedicated nature is provided for repeated docking of a male luer connector, wherein the docking apparatus facilitates the maintenance of sterility of the male luer connector when docked.

In the later regard, the defined arrangement facilitates the application of an anti-bacterial material to a top surface of the depressible member prior to each occasion upon which a male luer connector is docked. For such purposes, the top surface is preferably disposed one of substantially coplanar with or slightly bulging outward relative to a surrounding rim of the holding receptacle prior to/after docking of a male luer connector. Further, the depressible member may be advantageously provided to substantially fill and seal the single access opening during periods of non-use (e.g. prior to and after docking), wherein the depressible member effectively isolates the internal chamber from contamination during such periods. Moreover, the top surface is preferably continuous across the lateral extent thereof, e.g. free from slits, pores or other liquid passageways therethrough.

To provide a depressible member having the desired attributes, the depressible member should be of a resilient nature, e.g. at least partially compressible and/or deflectable within the holding receptacle, and should display a relatively high memory. By way of example, the depressible member may be integrally defined by an elastomeric material (e.g. silicon rubber or rubber foam). Further, an interconnected top layer may be utilized to separately define the top surface of the depressible member (e.g. a polymeric film such Mylar). In another approach, the depressible member may comprise an elastomeric part at a top end and a wire spring (e.g. a coil spring) at a bottom end.

Preferably, the holding receptacle and the depressible member are configured so that the depressible member is retained, or captured, within the internal chamber of the holding receptacle. In one approach, the single access opening of the holding receptacle may have a cross-dimension that is less than a corresponding cross-dimension of the top end of the depressible member (e.g. an inward edge of a surrounding receptacle rim defining the opening may overlap an outer edge portion of the top end of the depressible member). In another approach, the internal chamber and the depressible member may be sized and otherwise configured to have complimentary sidewall portions which are larger in cross-section than their respective top ends, wherein the sidewalls of each interface to retain the depressible member within the holding receptacle. For example, the sidewalls of the depressible member and internal chamber may have complimentary shoulder portions (e.g. stepped-out), wherein the sidewalls of the internal chamber restrain the depressible member within the internal chamber of the holding receptacle.

As noted, the holding receptacle of the docking apparatus is adapted for retentive engagement with a male luer connector end. In a primary approach, such functionality may be provided by defining a female luer connector about the single access opening of the holding receptacle. That is, complementary threaded surfaces may be utilized to facilitate ready interconnection/disconnection upon relative rotational movement of a male luer connector and the holding receptacle. Further, the single access opening of the holding receptacle may be preferably sized and configured to sealably engage the outside surface of a tapered nozzle of a male luer connector inserted thereinto.

The inventive docking apparatus may further include at least one handling member extending away from the holding receptacle to facilitate grasping and manipulation of the docking apparatus. Specifically, a lateral handling member may be provided that extends about and laterally away from the holding receptacle. Preferably, top and bottom portions of the holding receptacle extend upward and downward, respectively, from a lateral handling member. As an alternative or in addition to the lateral handling member, a rearward handling member may be provided that extends rearwardly from the holding receptacle. The rearward handling member may be of fin-like configuration to facilitate grasping by the fingers of a user as the docking apparatus and a male luer connector are rotated relative to one another for interconnection/disconnection. To yield enhanced torque, the rearward handling member may be of a width that is greater than that of the holding receptacle.

In conjunction with the noted features, the inventive docking apparatus may also include at least one slot sized for selective supportive interconnection of the docking apparatus to a tubing line at a patient site. Preferably, at least two slots are provided, wherein a tortuous path for tubing line engagement is defined therebetween and/or wherein two slots restrain tubing line movement in different directions (e.g. side-to-side and up-and-down). Most preferably, a tortuous path is defined that extends through more than one plane.

In one approach, a lateral slot(s) may be defined between the bottom of a lateral handling member and an inverted T-shaped member that defines a bottom portion of the holding receptacle. In such approach, the T-shaped member may be interconnected to a cylindrical top member to combinatively define the holding receptacle, wherein the depressible member is disposed therebetween. Additionally, one or more leg slots may be provided between legs that extend from the bottom of the lateral handling member, wherein each leg slot is defined by a different pair of legs. In one arrangement, leg slots are provided between opposing legs at each end of the docking apparatus and an intermediate, ring-shaped lateral slot is provided around the bottom portion of a cylindrical holding receptacle, wherein a straight-180° curve-straight pathway is defined for tubing line interconnection.

In another approach, one or more leg slots may be provided together with one or a plurality of edge slots provided about the periphery of a lateral handling member. In one arrangement leg slots are provided at each end of the docking apparatus and two edge slots with an intermediate side bar are provided on each side of the docking apparatus, wherein a straight-90° curve-180° curve-90° curve-straight pathway is defined which extends in more than one plane. Further, the leg slots may be provided to extend through a lateral handling member, wherein a wide range of tubing line approach angles can be realized.

As may be appreciated, the present invention also provides an inventive method for handling a male luer connector interconnected or interconnectable to a medical liquid source in connection with medical liquid administration procedures. In the broadest sense, the method includes the steps of administering medical liquid from the medical liquid source and, after such administration, docking the male luer connector with a docking apparatus. In primary applications, the administering step may entail attaching the male luer connector to an access port that is fluidly interconnected to a patient's vascular system (e.g. via a vascular catheter), and detaching the male luer connector from the access port following medical liquid administration.

In conjunction with the docking step, the method may include the docking sub-steps of contacting a nozzle of the male luer connector with the top surface of a depressible member disposed within a holding receptacle of the docking apparatus, and interconnecting the male luer connector with the holding receptacle, wherein the nozzle depresses the depressible member and is isolated in the holding receptacle. For such purposes the holding receptacle preferable has a single access opening thereinto. When repeated administration of medical liquid from the source is desired, the method further includes the step of disconnecting the male luer connector from the holding receptacle, and successively repeating the administering, docking and disconnecting steps. As may be appreciated, when repeating the administering step the vascular catheter access port may be contacted with anti-bacterial material prior to attachment of the male luer connector. For such purposes, the access port is preferably of a swabbable female luer type.

The docking step may further include the sub-step of applying an anti-bacterial material on the top surface of the depressible member prior to the noted contacting sub-step. By way of example, the anti-bacterial material may be applied by simply swabbing the anti-bacterial material onto the top surface of the depressible material (e.g. utilizing gauze swabs or the like). Relatedly, the contacting sub-step may provide for the engagement of a leading edge of the male luer connector nozzle with the top surface of the depressible member across the substantial entirety of such leading edge. Further, the noted engagement (i.e. between the leading edge of the nozzle and the top surface of the depressible member) may preferably be maintained during docking (e.g. to seal the nozzle). In conjunction with the docking step, the method may also preferably provide for sealing engagement between the holding receptacle and outer surface of the male luer connector nozzle. More particularly, the single access opening of the holding receptacle may be sized and configured to slidably, matingly receive a tapered nozzle of the male luer connector during docking.

For purposes of completing the docking and/or disconnecting steps, the method may further provide for the grasping of a handling member interconnected to the holding receptacle. For example, a lateral handling member may be held by a user and/or a reward handling member may be gripped by a user during connection/disconnection, wherein the holding receptacle and male luer connector may be advanced into or retracted from interconnection. In a primary approach, at least one of the holding receptacle and male luer connector may be rotated relative to the other to obtain a threaded interconnection/disconnection therebetween. To enhance the convenience of use and otherwise maintain an orderly patient care site, the method may further include the step of attaching a handling member of the docking device to a tubing line present at a patient site. For such purposes, the tubing line may be positioned through one or a plurality of interconnection slots provided by the docking apparatus. In one approach, such positioning may entail the routing of the tubing line between interconnection slots that define a tortuous path that extends through at least one and preferably more than one plane.

Additional aspects and advantages of the present invention will become apparent to one skilled in the art upon consideration of the further description that follows.

DETAILED DESCRIPTION

Figure 1A:
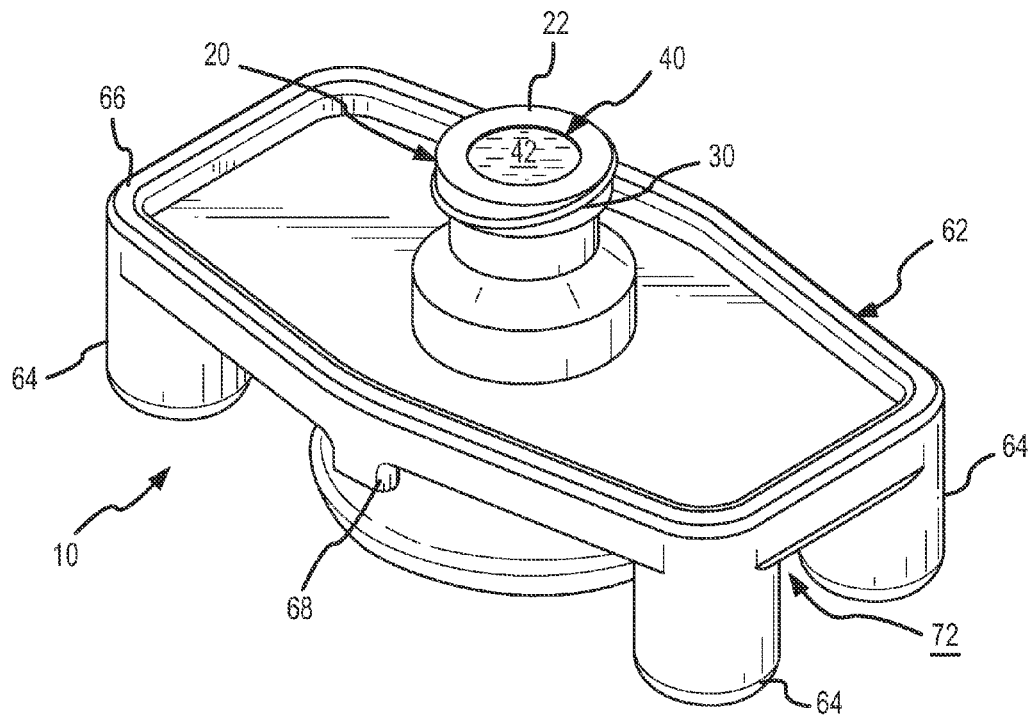
FIGS. 1A and 1B illustrate perspective and cross-sectional side views, respectively, of one docking apparatus embodiment of the present invention.
Figure 1B:
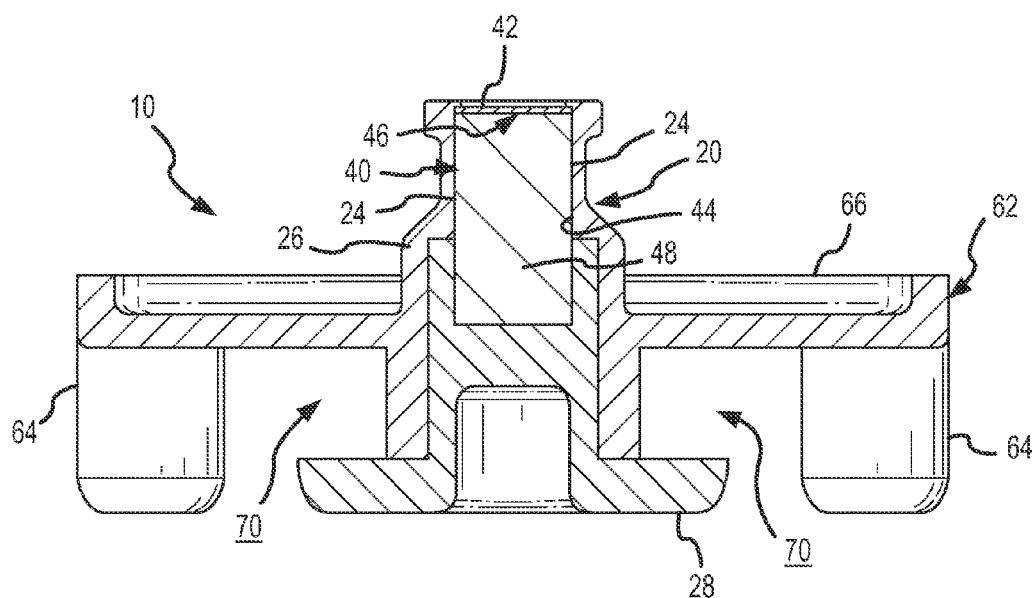
Figure 2A:
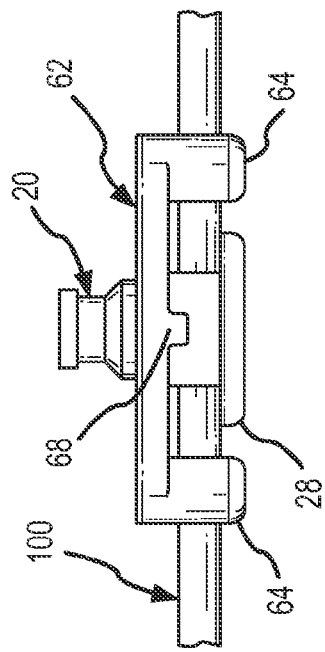
FIGS. 2A, 2B, 2C and 2D illustrate perspective, side, end and bottom views, respectively, of the docking apparatus embodiment of FIGS. 1A and 1B as interconnected to a tubing line.
Figure 2B:
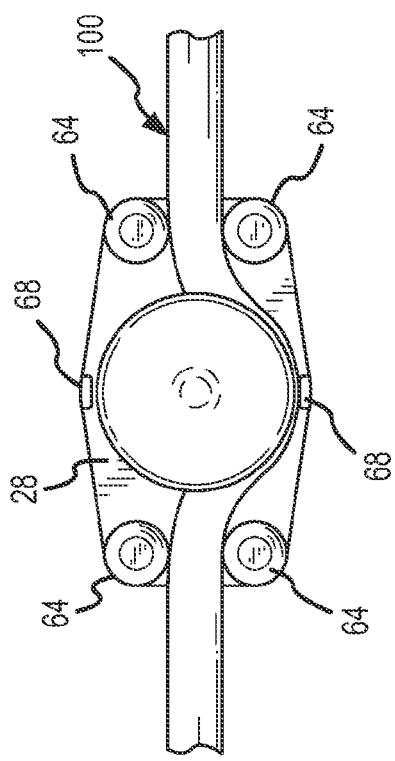
Figure 2C:
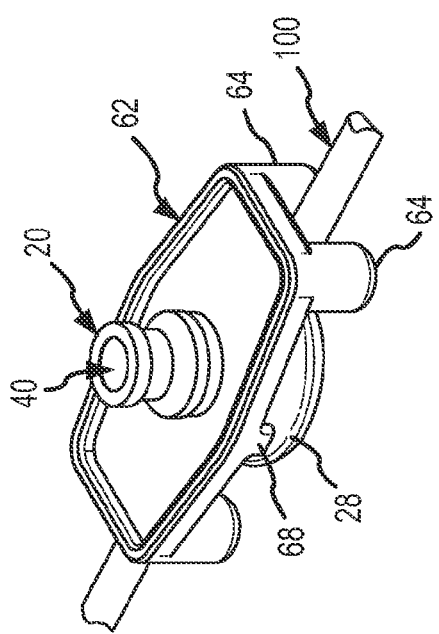
Figure 2D:
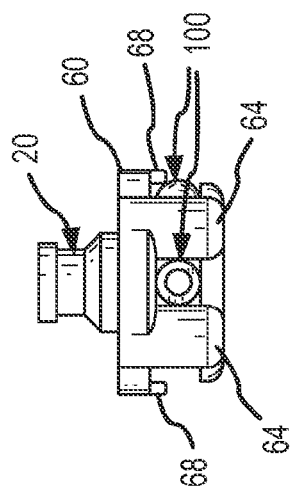

FIGS. 1A and 1B illustrate one embodiment of a docking apparatus 10 comprising the present invention. The docking apparatus 10 includes a holding receptacle 20 having a single access opening to an internal chamber with a depressible member 40 positioned therewithin. The holding receptacle 20 is adapted to retentively engage a male luer connector that is fluidly interconnected or interconnectable to a medical liquid source, wherein the depressible member 40 is depressed within and a nozzle of the male luer connector is isolated within the internal chamber of the holding receptacle 20 (i.e. via the single access opening) during docking.

As best shown by FIG. 1A, depressible member 40 may be disposed so that a top end thereof is located in and substantially fills the single access opening to the internal chamber of receptacle 20. More particularly, prior to/after docking a top surface 42 at the top end of depressible member 40 may be disposed one of substantially coplanar with or slightly bulging outward relative to a rim 22 of receptacle 20 that surrounds and thereby defines the single access opening, wherein the depressible member 40 seals off the access to the internal chamber of the holding 20 receptacle during non-use. Additionally, the holding receptacle 20 and depressible member 40 may be configured so that the depressible member 40 is retained in the internal chamber of holding receptacle 20.

To yield such an arrangement, the top end of depressible member 40 may be of a width that is less than a corresponding width of the single access opening of receptacle 20, wherein the inward edge of rim 22 captures the depressible member 40 in the internal chamber of the holding receptacle 20. Additionally, depressible member 40 may be of a length that is slightly greater than a depth of the internal chamber of holding receptacle 20, wherein the depressible member 40 may be slightly depressed as captured within holding receptacle 20 with the top surface 42 slightly bulged outward in the single access opening.

In this embodiment, the depressible member 40 may have an external configuration that is substantially coincident with the configuration of the internal chamber of holding receptacle 20. Further, the depressible member 40 may be sized to substantially fill the internal chamber. Specifically, the sidewalls 44 of depressible member 40 and internal sidewalls 24 of receptacle 20 may define substantially coincident cylindrical configurations as shown.

Certainly, other coincident configurations are possible, including configurations in which depressible member 40 and the internal chamber of holding receptacle 20 have coincident mid-portion or bottom-end widths which are greater than coincident top end widths. For example, such coincident configurations may include frusto-conical, or stepped-in sidewalls portions (e.g. to define coincident bottle-like configurations), wherein the depressible member 40 is captured in the internal chamber by restraining interface between the internal sidewalls of the holding receptacle 20 and external sidewalls of the depressible member 40.

In the illustrated embodiment, holding receptacle 20 is defined by a top member 26 and interconnected bottom member 28. By way of example, the top and bottom members 26, 28 may be provided for selective snap-fit engagement, wherein the depressible member 40 may be interposed therebetween prior to connection. In other arrangements, the top and bottom members 26, 28 may be hingedly interconnected or provided with complimentary threading for screw-type interconnection. Alternatively, receptacle 20 may be a one-piece construction, wherein depressible member 40 is forcibly inserted in a slightly depressed, or compressed, state upon assembly.

As may be appreciated, depressible member 40 should be of a resilient nature, wherein the depressible member 40 is capable of both being depressed during docking and returning to its initial configuration to substantially fill and seal the single access opening of holding receptacle 20 after docking. For example, in the embodiment of FIGS. 1A and 1B, the depressible member 40 may be integrally defined by a compressible material. By way of example, such compressible material may comprise a molded elastomeric foam (e.g. a closed or open cell rubber foam).

The top surface 42 of the depressible member 40 may be integrally defined by a compressible material as described above. Alternatively, the top surface 42 may be defined by a top layer 46 adjoined to the top end of a main body. By way of example, the top layer may comprise a polymeric film (e.g. Mylar). In either case, the provision of a substantially continuous, non-porous top surface 42 facilitates the application of an anti-bacterial material thereto prior to docking of the apparatus 10 with a male luer connector.

For purposes of retentive docking, the top end of holding receptacle 20 should may be sized and preferably provided with external threads 30 that are compatible for selective threaded engagement with complimentary threads disposed on male luer connectors. Further, to facilitate sealed docking, the single access opening of the holding receptacle may be sized and configured to slidably, matingly receive a tapered nozzle of the male luer connector during docking. In this regard, docking apparatus 10 may be provided for universal use with any medical liquid source that is fluidly interconnected or interconnectable with a compatible male luer connector.

Referring further to FIGS. 1A and 1B, the docking apparatus 10 may include a lateral handling member 62 having legs 64 interconnected thereto. The lateral handling member 62 extends around and laterally away from the sides of holding receptacle 20, thereby providing a convenient means for grasping and manipulating the docking apparatus 10. As shown, the lateral handling member 62 may be integrally defined with the top member 26 of holding receptacle 20 (e.g. via a plastic molding). The top end of the holding receptacle 20 extends upwardly from, and the legs 64 and bottom end of holding receptacle 20 extend downwardly from the lateral member 62, respectively. To facilitate docking procedures the topside of the lateral member 62 may be provided with a peripheral rim 66. Downward-extending tabs 68 may also be provided on opposing side edges of the lateral member 62 to enhance interconnection of the docking apparatus 10 with a tubing line at a patient care site.

In this regard, docking apparatus 10 may include a number of slots sized and located for selective receipt of a tubing line. In particular, a lateral slot 70 may be provided on the bottom side of the lateral handling member 60. In the illustrated embodiment slot 70 is defined between the bottom side of lateral member 62 and a ring-shaped portion of the bottom member 28. In this regard, the bottom member 28 may have an inverted T-configuration (i.e. as interconnected to the top member 26). Legs 64 may also define leg slots 72 at each end of the docking apparatus 10. Such leg slots 72, together with lateral slot 70, may be sized to retainably engage and otherwise define a tortuous path for an interconnected tubing line.

More particularly, and with reference now to FIGS. 2A-2D an exemplary tubing line 100 is shown interconnected to docking apparatus 10. As illustrated, the leg slots 72 disposed at each end of the docking apparatus 10 are sized to matingly receive the tubing line 100 therebetween. Further, slot 70 is sized to matingly receive the tubing line 100 as it follows a curved path around a cylindrical portion of bottom member 28. That is, slots 70, 72 collectively define a straight-180° curve-straight path for tubing line interconnection. Finally, tabs 68 of handling member 60 may be sized and spaced away from bottom member 28 to allow selective positioning of tubing line 100 around the cylindrical portion of the bottom member 28, while also providing a lateral retentive interface therewith.

Figure 3A:
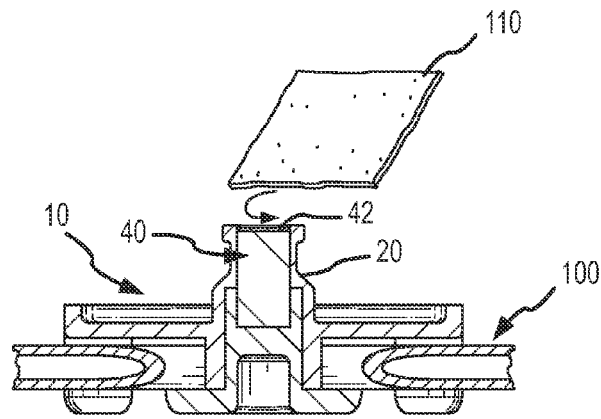
FIGS. 3A, 3B and 3C are side cross-sectional views illustrating an exemplary use of the embodiment of FIGS. 1A and 1B.
Figure 3B:
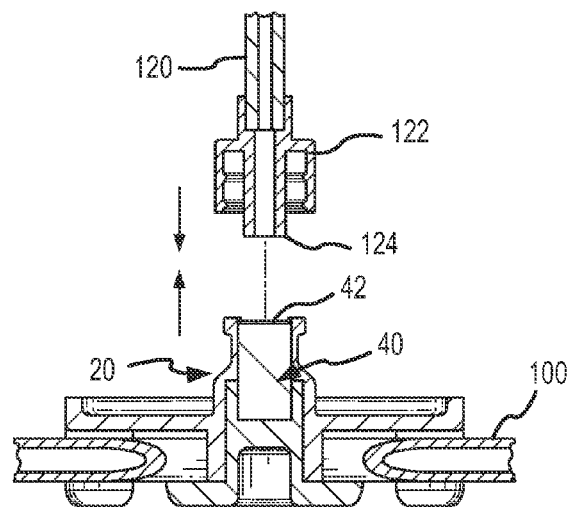
Figure 3C:
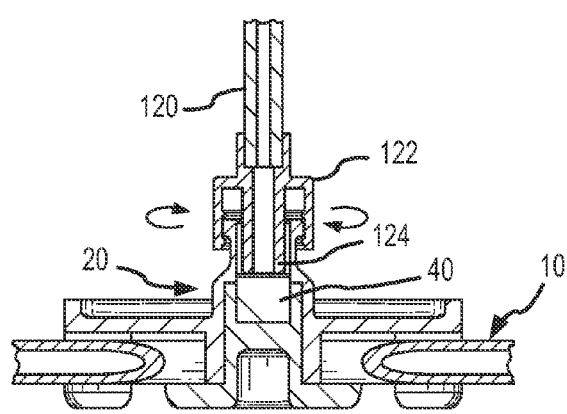

FIGS. 3A-3C illustrate an exemplary use of docking apparatus 10. In particular, FIG. 3A illustrates docking apparatus 10 interconnected to an exemplary tubing line 100, e.g. at a patient site. FIG. 3A further illustrates the application of an anti-bacterial material onto the top surface 42 of depressible member 40 via use of a swab 110. By way of example, swab 110 may be of a premoistened type (i.e. moistened with an antibacterial material and packaged in a tear-open foil pouch).

Moving to FIG. 3B, an exemplary male luer connector 122, fluidly interconnected or interconnectable via tubing line 120 with a medical liquid source, is shown in an aligned position with the single access opening of holding receptacle 20 of docking apparatus 10. To proceed with docking, the male luer connector 122 and/or docking apparatus 10 are advanced relative to one another so that the nozzle 124 of the male luer connector 122 engages the top surface 42 and the anti-bacterial material applied thereupon.

Referring now to FIG. 3C, the male luer connector 122 has been retentively engaged by holding receptacle 20, e.g. via threaded engagement by relative rotation of the male luer connector 122 and the holding receptacle 20. As shown, the depressible member 40 is resiliently compressed within the internal chamber of holding receptacle 20, wherein the nozzle 124 of the male luer connector 122 is isolated within and engaged with the top surface 42 of depressible member 40 within the holding receptacle 20. In this regard, the top surface 42 of depressible member 40 may resiliently engage the leading edge of the nozzle 124 substantially continuously across the lateral extent thereof to facilitate sealing. Additionally, the inside edge of rim 22 may slidably receive and thereby sealably engage an outer tapered surface of the nozzle 124 of the male luer connector 120.

As will be appreciated, the male luer connector 122 may be maintained in the illustrated docked position of FIG. 3C until medical liquid administration to a patient is desired. To achieve disconnection, the male luer connector 122 may be simply rotated out of threaded engagement with the holding receptacle 20. Upon such disconnection, the depressible member 40 may preferably return to the same or substantially the same configuration shown in FIGS. 3A and 3B, wherein access to the internal chamber of holding receptacle 20 is substantially precluded. After medical liquid administration, the male luer connector 122 may be redocked with the docking apparatus 10 following the same procedure described above in relation to FIGS. 3A-3C. Such procedure may be successively repeated as desired.

Figure 4A:
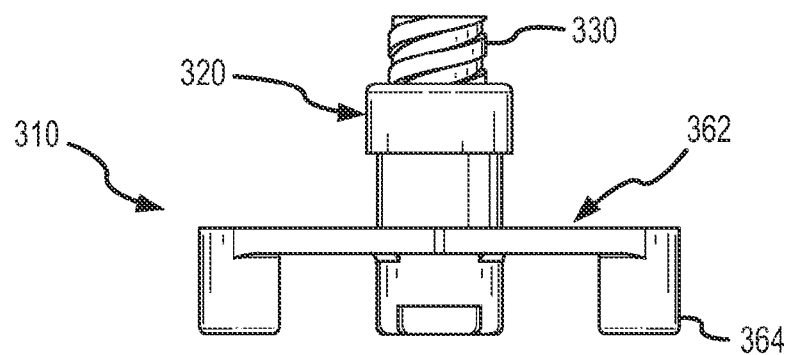
FIGS. 4A, 4B, 4C, 4D and 4E illustrate side, end, side cross-sectional, bottom and top views, respectively, of another docking apparatus embodiment of the present invention.
Figure 4B:
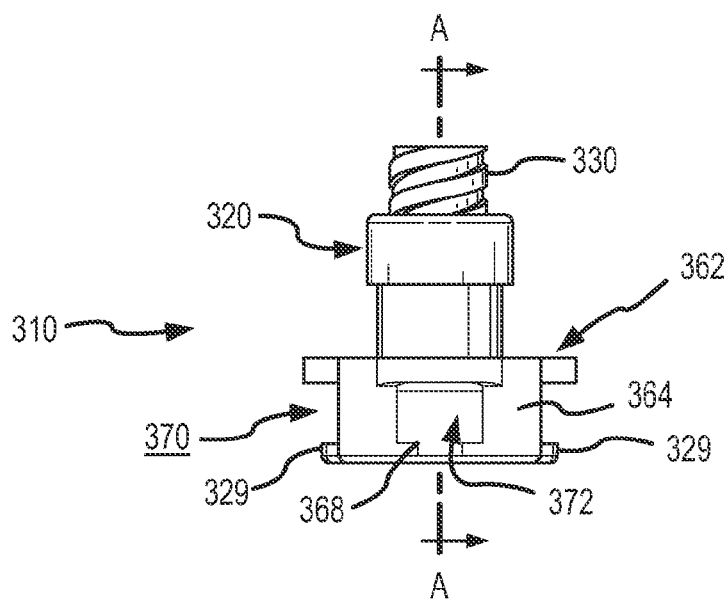
Figure 4C:
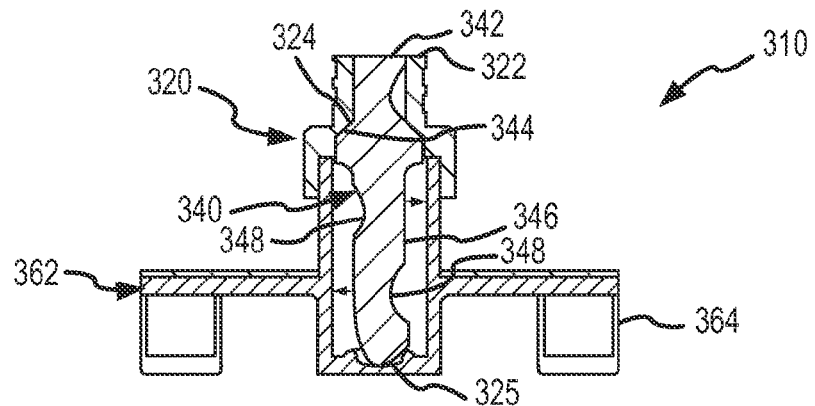
Figure 4D:
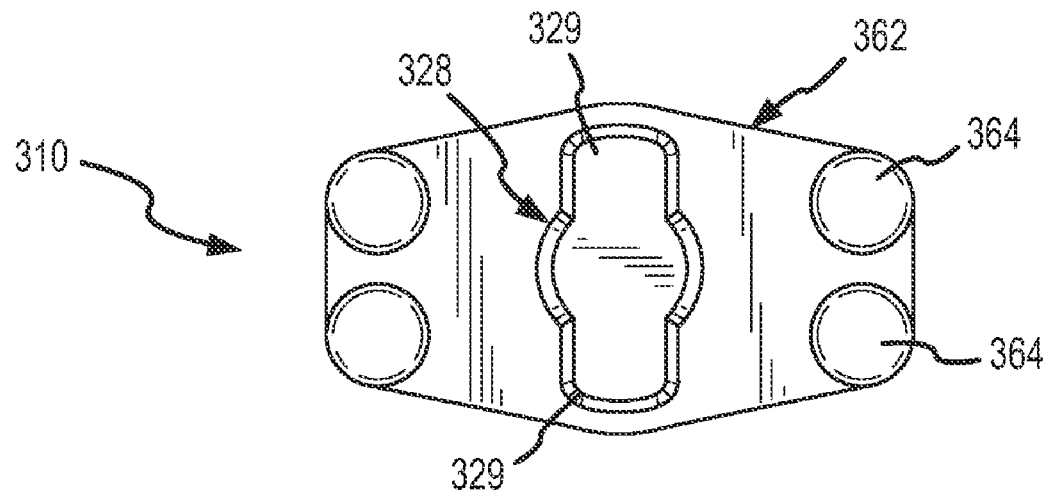
Figure 4E:
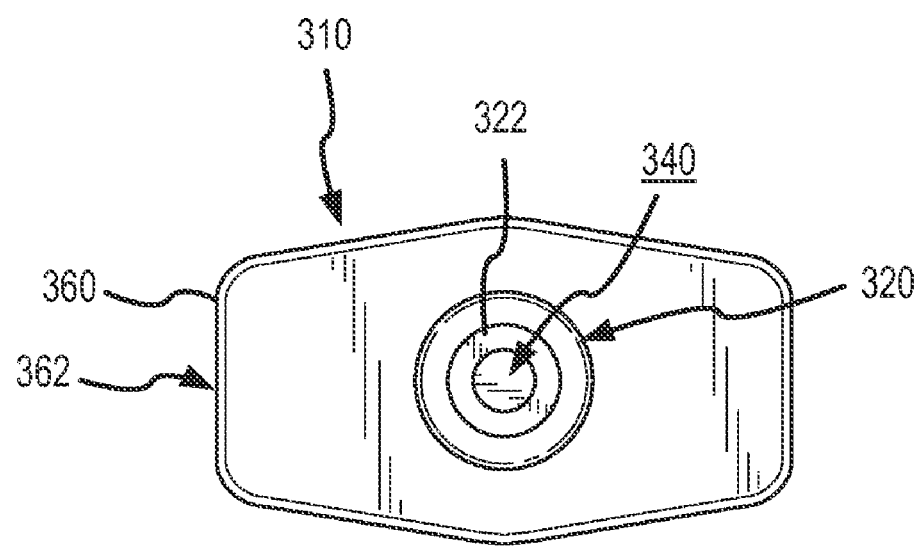

FIGS. 4A-4E illustrate another embodiment of docketing apparatus 310 comprising the present invention. The docking apparatus 310 includes a holding receptacle 320 having an internal chamber with depressible member 340 positioned therewithin. As illustrated by FIG. 4C, depressible member 340 is disposed so that top end thereof is located within, substantially fills and thereby seals a single access opening to the internal chamber of receptacle 320 prior to and after docking with a male luer connector. Further, a top surface 342 of the depressible member 340 is disposed in one of substantially coplanar relation with or to slightly bulge out way relative to a rim 322 of receptacle 320 prior to/after docking.

As shown in FIG. 4C, a shouldered-sidewall portion 344 of depressible member 340 is provided for retentive engagement by a substantially coincidental shouldered-sidewall portion 324 of receptacle 320 prior to/after docking. Of note, body portion 346 of depressible member 340 is sized (e.g. in cross-width) and otherwise adapted to facilitate deflection, or bowing, of such body portion 346 within the internal chamber of holding receptacle 320 upon docking of a nozzle of a male luer connector within the single access opening of receptacle 320. That is, when the nozzle of a male luer connector contacts the top surface 342 of the depressible member 340 and is advanced into the single access opening of the holding receptacle 320 the body portion 346 of the depressible member 340 is provided to buckle or bow away from a center axis of the holding receptacle 320 as the depressible member 340 is advanced within the internal chamber. To facilitate such functionality, one or more surface discontinuities 348 (e.g. cut-out or scalloped regions) may be provided on the body portion 346 of the depressible member 340. Further, a positioning seat 325 may be provided at the bottom of the internal chamber of receptacle 320 so as to locate a bottom end of the depressible member 340 on the center axis of the receptacle 320. In one arrangement, the depressible member 340 comprises a molded elastomeric material (e.g. silicon rubber) that deflects upon docking and resiliently returns to the same or substantially the same configuration shown in FIG. 4C after docking.

As further shown by FIG. 4C, the holding receptacle 320 is defined by a top member 326 and bottom member 328. By way of example, the top and bottom members 326, 328 may be provided for selective snap-fit engagement or may be glued together upon assembly with the depressible member 340 positioned therebetween within the internal chamber of holding receptacle 320. To facilitate retentive docking, the top end of the holding receptacle may be stepped-in, sized and provided with threads 330 compatible for selective threaded engagement with complimentary threads disposed on male luer connectors.

The docking apparatus 310 may further include a lateral handling member 362 which having corner legs 364 interconnected thereto. The lateral handling member 362 extends about and laterally away from the sides of holding receptacle 320 to facilitate handling of the docking apparatus 310. In this embodiment, the handling member 360 is integrally defined with the bottom member 328 of the holding receptacle 320 (e.g. via plastic molding) and a top layer 360 may be secured (e.g. glued) on the lateral handling member 362. As shown, the top end of holding receptacle 320 extends upwardly from the lateral member 362 and the corner legs 364 and bottom end of holding receptacle 320 extend downwardly from the lateral member 362. A top side of the lateral member 362 may be provided with a peripheral rim 366.

Docking apparatus 310 may be provided with lateral slots 370 for selective receipt of a tubing line at a patient site. The lateral slots 370 are provided on a bottom side of the lateral handling member 360 between the bottom side of the lateral member 362 and wing-like projections 329 extending from opposing sides of the bottom member 328. As shown by FIG. 5D, the bottom member 328 again may be of an inverted T-configuration (i.e. as interconnected to the top member 326). In addition to lateral slots 370, leg slots 372 may be provided by corner legs 364 for tubing line engagement. To further enhance tubing line interconnection, the legs 364 may include flanges 368, wherein the flanges 368 of opposing leg members 364 define a reduced slot opening.

Figure 5A:
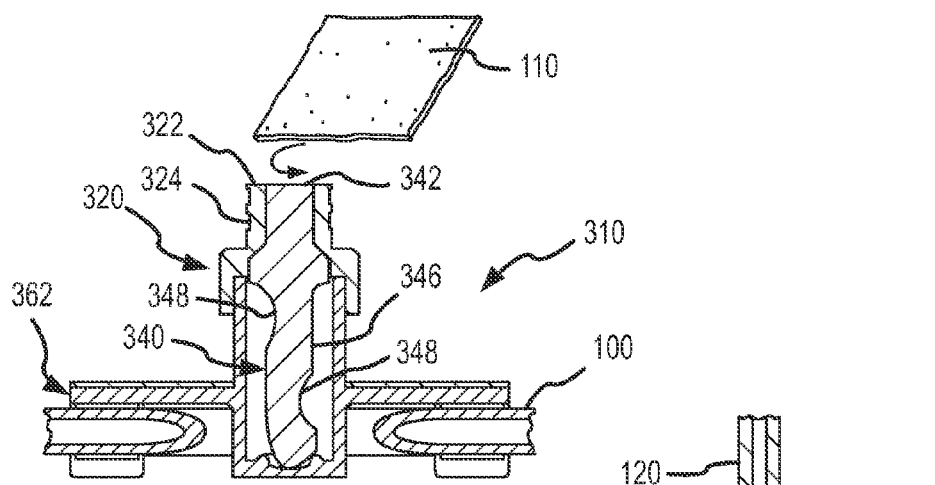
FIGS. 5A, 5B and 5C are side cross-sectional views illustrating an exemplary use of the embodiment of FIGS. 4A-4E.
Figure 5B:
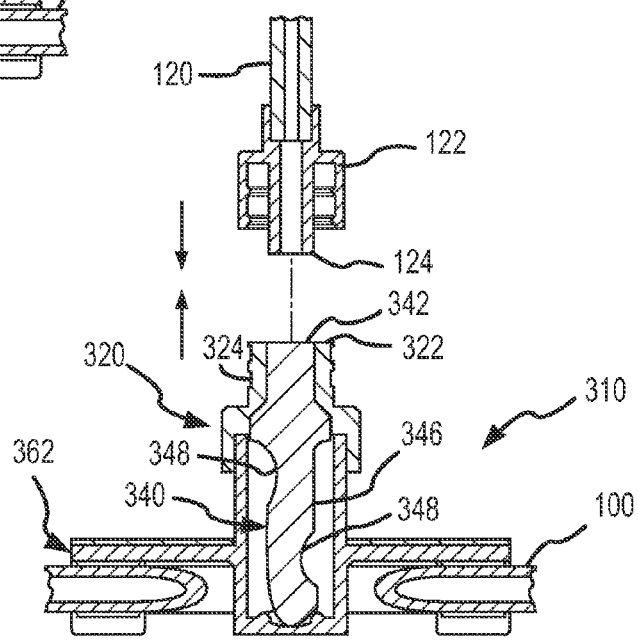
Figure 5C:
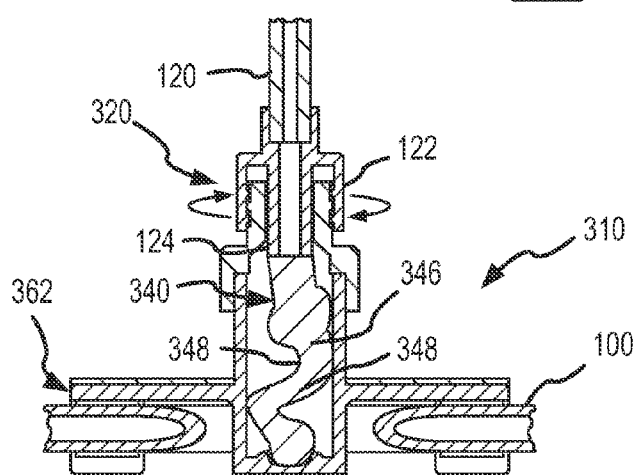

FIGS. 5A-5C an exemplary use of docking apparatus 310. As shown, the docking apparatus 310 is interconnected to an exemplary tubing line 100, e.g. at a patient site. In FIG. 5A, an antibacterial material is being applied to the top surface 342 of the depressible member 340 via use of a swab 110. In FIG. 5B an exemplary male luer connector 122, fluidly interconnected or interconnectable via tubing line 120 with a medical liquid source, is shown in an aligned position with the single access opening of the holding receptacle 320 of the docking apparatus 310. To proceed with docking, the male luer connector 122 and/or docking apparatus 310 are advanced relative to one another so that the nozzle 124 of the male luer connector 122 engages the top surface 342 and the antibacterial material applied thereupon.

In FIG. 5C the male luer connector 122 is retentively engaged by holding receptacle 320, e.g. via the threaded engagement by relative rotation of the male luer connector 122 and the holding receptacle 320. As shown, the depressible member 340 is resiliently deflected within the internal chamber of the holding receptacle 320, wherein the nozzle 124 of the male luer connector 122 is isolated within and engaged with the top surface 342 of the depressible member 340 within the holding receptacle 320. In this regard, the top surface 342 of the depressible member 340 may resiliently engage the leading edge of the nozzle 124 substantially continuously across lateral extent thereof to facilitate sealing. Additionally, the inside edge of rim 322 may slidably receive and thereby sealably engage an outer tapered surface of the nozzle 124 of the male luer connector 120.

The male luer connector 122 may be maintained in the illustrated docked position of FIG. 5C until medical liquid administration to patient is desired. At that point, the male luer connector 122 may be simply rotated out of threaded engagement with the holding receptacle 320. Upon such disconnection, the depressible member 340 may be preferably return to the same or substantially the same configuration shown in FIGS. 5A and 5B, wherein access to the internal chamber of holding receptacle 320 is substantially precluded. After medical liquid administration, the male luer connector 122 may be redocked with the docking apparatus 320 following the same procedure described above in relation to FIGS. 5A-5C. Such procedure may be successively repeated as desired.

Figures 6A, 6B:
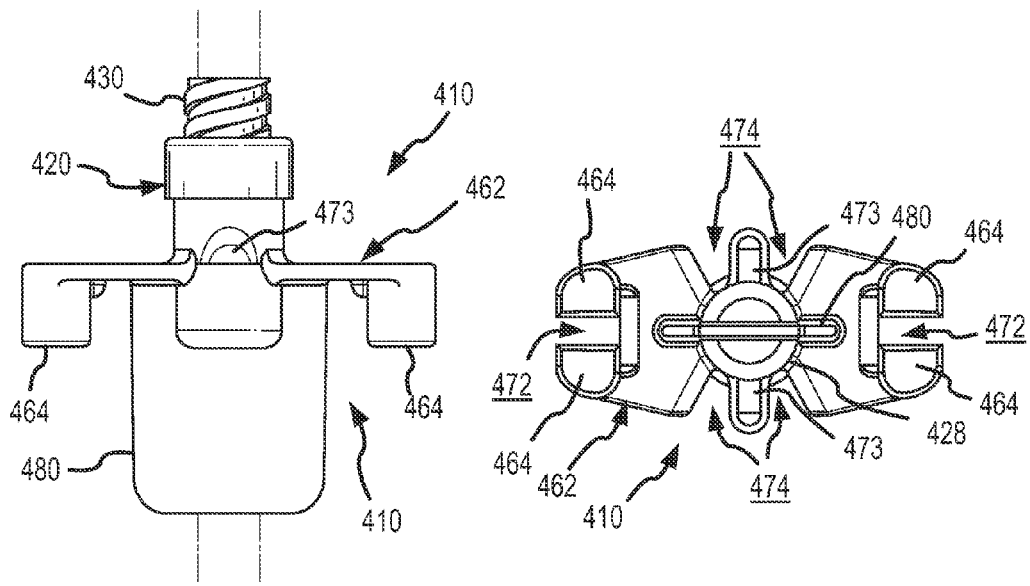
FIGS. 6A, 6B and 6C illustrate side, bottom and top views, respectively, of another docking apparatus embodiment of the present invention.
Figures 6C, 6D:
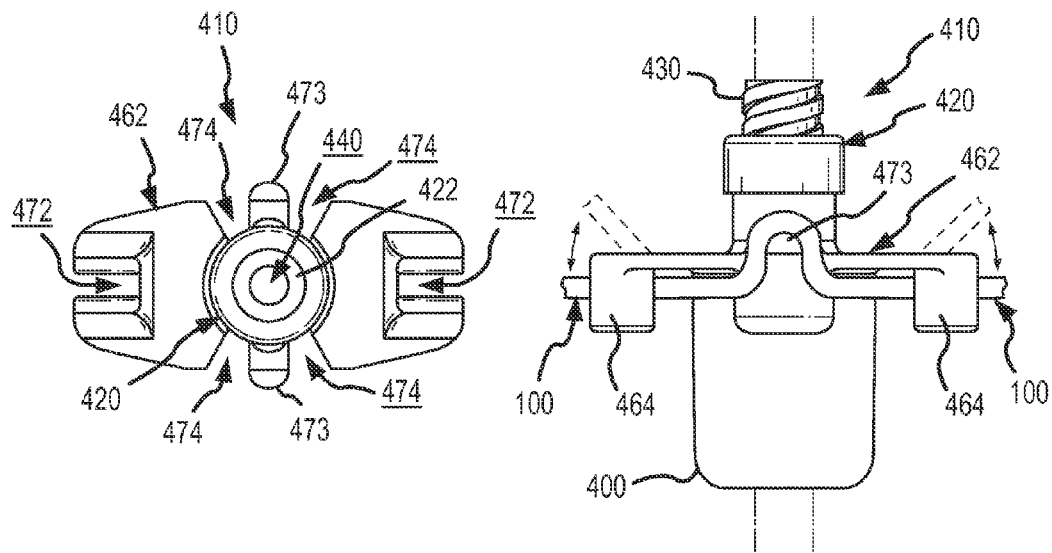
FIG. 6D illustrates a side view of the docking apparatus embodiment of FIGS. 6A-6C as interconnected to a tubing line.

FIGS. 6A-6C illustrate yet another embodiment of a docking apparatus 410 comprising the present invention. The docking apparatus 410 is quite similar to the docking apparatus 310 described in relation to FIGS. 4A-4E.

In particular, docking apparatus 410 includes a holding receptacle 420 having an internal chamber with a depressible member 440 positioned within an internal chamber thereof. The depressible member 440 substantially fills a single access opening to the internal chamber and is disposed one of substantially coplanar with and slightly bulging outward relative to a surrounding rim 422 of the single access opening prior to/after docking of a male luer connector. While not shown in cross-section, depressible member 440 is also sized and otherwise adapted to facilitate defection, or bowing, within the internal chamber of the holding receptacle 420 upon docking of a nozzle of a male luer connector within the single access opening to the internal chamber 420. Such functionality may be provided in the same manner as described in relation to the docking apparatus 310 of FIGS. 4A-4E.

The docking apparatus 410 may also include a lateral handling member 462 having corner legs 464 interconnected thereto. The lateral handling member 462 extends laterally away from opposing sides of the holding receptacle 420 to facilitate grasping and manipulate of the docking apparatus 410. Additionally, side-bars 463 may be provided on the holding receptacle 420, wherein edge slots 474 are defined between the lateral handling member 462 and side-bars 463 of docking apparatus 410. Edge slots 474 may be utilized for selective interconnection of the docking apparatus 410 to a tubing line at a patient site. For such purposes, the docking apparatus 410 may further include leg slots 472 which are defined between opposing legs 464 and which further extend through the lateral handling member 460. Each of the various slots 472 and 474 may be sized for retention of a tubing line and beveled and/or tapered to facilitate non-occlusive interconnections.

As further shown by FIGS. 6A-6C, docking apparatus 410 also includes a rearward handling member 480 that extends rearwardly from the holding receptacle 420. As shown, rearward handling member 480 may be of a fin-like configuration and may be oriented co-axially with leg slots 472. Of note, the rearward handling member 480 may have a width that is greater than that of the holding receptacle 420. Further, rearward handling member 480 may have a center axis aligned with that of the holding receptacle configuration of rearward handling member 480. The noted configuration features of rearward handling member 480 facilitates ready grasping by the fingers of a user, wherein enhanced torque may be applied during connection/disconnection of the docking apparatus 410 to a male luer connector.

Referring now to FIG. 6D, docking apparatus 410 is shown interconnected to a exemplary tubing line 100. As will be appreciated, such tubing line 100 may be present at a patient care site and provides a convenient means for supporting and locating the sterile docking apparatus 410. In this regard, the various slots 472 and 474 of docking apparatus 410 provide a number of options for interconnection with tubing line 100. In the arrangement shown in FIG. 6D, the tubing line 100 has been positioned to pass through the leg slots 472 and over side-bar 463 through edge slots 474 on one side of the docking apparatus 410. As may be appreciated, this arrangement yields a straight-90° curve-180° curve-90° curve-straight path for interconnection of tubing line 100 that extends in more than one plane, thereby enhancing the reliability of interconnection. Relatedly, by providing leg slots 472 that extend through the lateral member 462, an enhanced range of approach angles by tubing line 100 may be accommodated, thereby further facilitating interconnection.

Figure 7:
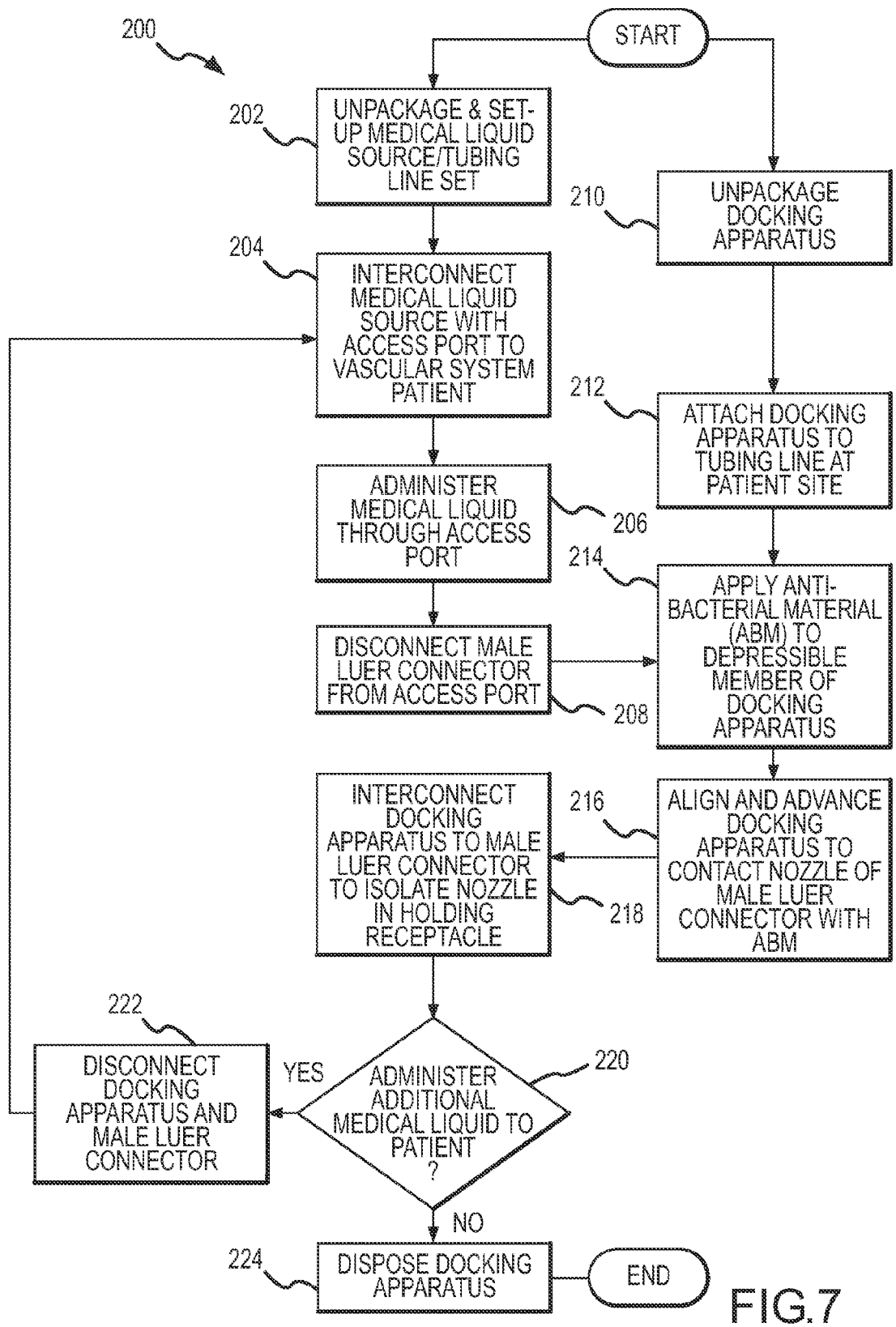
FIG. 7 is a flow diagram illustrating one method embodiment of the present invention.

In view of the foregoing embodiments, it will be appreciated that an overall method for use in conjunction with medical liquid administration is facilitated. To describe such method, reference is now made to the method embodiment 200 illustrated in FIG. 7.

As shown, method embodiment 200 may include the initial step of unpackaging and setting up a medical liquid source and tubing line set (step 200). By way of example, the medical liquid source and tubing line set may comprise a vessel (e.g. a bag, syringe or vial) containing a medical liquid (e.g. liquid medication or flush solution), and a tubing length interconnected or interconnectable to the vessel at a proximal end and having a male luer connector at a distal end. In another arrangement, the tubing line set may further include a separate means for transferring liquid from the vessel through the tubing length.

Next, the medical liquid source may be interconnected to an access port to the vascular system of a patient (step 204). More particularly, a vascular catheter may be inserted into the vein of a patient and provided with an interconnected access port in the form of a female luer connector (e.g. preferably a swabbable type). Such female luer connector end may then be selectively interconnected with a male luer connector of the tubing line set that is interconnected with the medical liquid source. Upon such interconnection, medical liquid may be administered through the male luer connector end and female luer connector end into the patient via the vascular catheter (step 206).

After a desired amount of medical liquid has been administered, the male luer connector may be selectively disconnected from the access port (step 208). Prior to or in conjunction with such disconnection, a docking apparatus as described above may be removed from sterile packaging (step 210). Further, such docking apparatus may be supportably attached to a tubing line at the patient care site (step 212). Such attachment may entail the routing of the tubing line through one or more slots of the docking apparatus as noted above. Then, prior to docking the male luer connector with the docking apparatus, an anti-bacterial material (ABM) may be applied to a top surface of a depressible member presented by the docking apparatus (step 214).

In docking the male luer connector, the connector and docking apparatus may be aligned and advanced towards each other so that the nozzle of the male luer connector contacts the ABM on the top surface of the docking apparatus (step 216). The male luer connector and docking apparatus may then be interconnected (e.g. via threaded engagement) to isolate the nozzle of the male luer connector end within the holding receptacle of the docking apparatus (step 218).

Additional medical liquid may be administering via disconnection of the male luer connector and docking apparatus (steps 220 and 222), and repetition of steps 206, 208, 214, 216, and 218 noted above. This sequence may be further repeated as desired. In conjunction with such procedure, the ABM may be applied to the noted vascular catheter access port prior to each interconnection thereof with the male luer connector of the tubing line set.

Of note, the same docking apparatus may be employed in conjunction with each repeated sequence of medical liquid administration and male luer connector docking, thereby avoiding the need for separate capping procedures after each use of the male luer connector. Upon depletion of a given medical liquid source or after a predetermined period of time-in-use a given medical liquid source and/or tubing line set may be selectively disposed. Further, prior to or upon completion of the medical liquid therapy for a given patient the docking apparatus may be disposed (step 224).

The embodiments described above are for exemplary purposes only and are not intended to limit the scope of the present invention. Various adaptations, modifications and extensions will be apparent to those skilled in the art. For example, certain aspects of the present invention may be implemented in a further simplified embodiment which includes a cylindrical holding receptacle having a depressible member restrainably disposed therein. One end of the holding receptacle may be provided with external threads (e.g. for male luer interconnection). The other end may be interconnected via internal or external threading to a cap member having complementary threading, thereby defining an internal chamber with a single access opening.

Such embodiment as well as others are intended to be within the scope of the invention as defined by the claims which follow.

What is claimed is:

1. A medical liquid administration method, comprising:
   administering a medical liquid to a patient from a medical liquid source through a fluidly-interconnected male luer connector, including:
   attaching the male luer connector to a female luer connector fluidly connected to a vascular catheter fluidly interconnected to the patient's vascular system;
   passing the medical liquid from the medical liquid source through the male luer connector and vascular catheter to the patient; and,
   detaching the male luer connector from the vascular catheter;
   docking the detached male luer connector to a docking apparatus having a holding receptacle with a single access opening, after the administering step, including:

contacting a nozzle of the male luer connector with a top surface of a resilient depressible member disposed within the single access opening of the holding receptacle; and, interconnecting the male luer connector with the holding receptacle, wherein the nozzle depresses the depressible member within and displaces all of the top surface of the depressible member relative to the single access opening of the holding receptacle, and wherein the nozzle is isolated within the holding receptacle of the docking apparatus throughout the docking step.

2. A method as recited in claim 1, wherein said depressible member is depressed from an initial configuration to a depressed configuration during the docking step, and wherein the method further comprises:

disconnecting the male luer connector from the holding receptacle of the docking apparatus after the docking step, wherein the depressible member resiliently returns to said initial configuration upon said disconnection.

3. A method as recited in claim 2, wherein said depressible member seals off access to said holding receptacle prior to said docking step and after said disconnecting step.

4. A method as recited in claim 2, wherein said depressible member substantially fills the said single access opening of said holding receptacle prior to said docking step and after said disconnecting step.

5. A method as recited in claim 2, wherein the top surface of the depressible member is substantially continuous and non-porous across the lateral extent thereof.

6. A method as recited in claim 5, wherein said docking step further comprises:

applying an anti-bacterial material to the top surface of the depressible member prior to said contacting sub-step.

7. A method as recited in claim 2, further comprising:

successively repeating said administering, docking and disconnecting steps.

8. A method as recited in claim 2, wherein said contacting step of said docking step includes:

engaging a leading edge of the nozzle of the male luer connector with said top surface of the depressible member across the entirety of the leading edge.

9. A method as recited in claim 1, wherein the docking step further comprises:

slidably engaging an outer tapered surface of the nozzle at said single access opening of the holding receptacle.

10. A method as recited in claim 1, wherein the docking step further comprises:

sealably engaging an outer tapered surface of the nozzle at said single access opening of the holding receptacle.

11. A method as recited in claim 1, wherein said depressible member and said holding receptacle are configured so that the depressible member is restrained by and within the holding receptacle.

12. A method as recited in claim 1, said interconnecting step of said docking step further including one of the following:

compressing said depressible member within an internal chamber of said holding receptacle; and, deflecting said depressible member within an internal chamber of said holding receptacle.

13. A method as recited in claim 12, wherein a bottom end of the depressible member engages the holding receptacle at a bottom of an internal chamber of the holding receptacle during at least the interconnecting substep of the docking step.

14. A method as recited in claim 1, said interconnecting step of said docking step including:

engaging said male luer connector with an outer surface of said holding receptacle of the docking apparatus; and, rotatably advancing at least one of said male luer connector and said holding receptacle of the docking apparatus relative to the other to obtain a threadable interconnection therebetween.

15. A method as recited in claim 1, wherein said docking step further includes slidably engaging an outer tapered surface of the nozzle at said single access opening of the holding receptacle, and further comprising:

disconnecting the male luer connector from the holding receptacle of the docking apparatus after the docking step, wherein the depressible member resiliently returns to said initial configuration upon said disconnection.

16. A method as recited in claim 15, said interconnecting substep of said docking step further including one of the following:

compressing said depressible member within an internal chamber of said holding receptacle; and, deflecting said depressible member within an internal chamber of said holding receptacle.

17. A method as recited in claim 16, wherein a bottom end of the depressible member engages the holding receptacle at a bottom of an internal chamber of the holding receptacle during at least the interconnecting substep of the docking step.

18. A method as recited in claim 17, said interconnecting substep of said docking step including:

engaging said male luer connector with an outer surface of said holding receptacle of the docking apparatus;

rotatably advancing at least one of said male luer connector and said holding receptacle of the docking apparatus relative to the other to obtain a threadable interconnection therebetween.

19. A method as recited in claim 18, wherein the top surface of the depressible member is substantially continuous and non-porous across lateral extent, and further comprising:

applying an anti-bacterial material to the top surface of the depressible member prior to said contacting sub-step.

20. A method as recited in claim 19, wherein said depressible member seals off access to said holding receptacle prior to said docking step and after said disconnecting step.

21. A method as recited in claim 20, wherein said depressible member and said holding receptacle are configured so that the depressible member is restrained by and within the holding receptacle.

22. A method as recited in claim 2, wherein the nozzle displaces all of the top surface of the depressible member within the single access opening of the holding receptacle in the interconnecting step of the docking step.

* * * * *